US00PP10063P

Jnited States Patent [19]

andenBerg

[11] Patent Number: Plant 10,063

[45] Date of Patent: Oct. 14, 1997

4] CARNATION PLANT NAMED BOURBON STREET

5] Inventor: Cornelis P. VandenBerg, Salinas, Calif.

3] Assignee: Yoder Brothers, Inc., Barberton, Ohio

1] Appl. No.: 608,625

2] Filed: Mar. 1, 1996

1] Int. Cl.[6] ..... A01H 5/00

2] U.S. Cl. ..... Plt./72.1

8] Field of Search ..... Plt./72.1, 71.1, Plt./73.1 imary Examiner—James R. Feyrer
sistant Examiner—Melissa L. Kimball

Attorney, Agent, or Firm—Foley & Lardner

[57] ABSTRACT

A carnation plant named Bourbon Street particularly characterized by its commercial double flower type; flat flower form; cerise-cherry flower color; diameter of flower of 77 to 84 mm when fully opened, when grown as a disbudded carnation; rounded petals, with serrated and slightly ruffled petal margins; heavy, strong stems; relatively fast flowering response of 23 to 26 weeks after planting rooted cuttings; tolerant to resistant to *Fusarium oxysporum;* high percentage of long to very long flowering stems from 45 to over 65 cm in length; and recommended as a standard (disbudded) carnation.

1 Drawing Sheet

1

The present invention comprises a new and distinct cul-'ar of carnation, botanically known as *Dianthus caryophyl-s* L. and referred to by the cultivar name Bourbon Street. Bourbon Street, identified as 2566 (89-262001), was iginated from a cross made under supervision of Cornelis VandenBerg in a controlled breeding program in Salinas, lif., in September of 1985.

The female parent of Bourbon Street was an unnamed edling identified as 0016 (82-501003), and described as a rk pink spray carnation.

The male parent of Bourbon Street was the cultivar entified as Desio, described as a red standard (disbudded) rnation.

The breeding program resulting in Bourbon Street had as ijective to create new carnation cultivars resistant to *isarium oxysporum.* In order to ensure resistance, seed-igs were planted in a controlled environment in soil avily infested with *Fusarium oxysporum* in Suba, near ogota, Colombia, South America. Seedlings were allowed grow to flowering stage, with removal of those seedlings at died from *Fusarium oxysporum.*

Bourbon Street was discovered and selected as one flowing plant within the progeny of the stated cross by Cornelis VandenBerg in October of 1989, in the above described cation.

The first act of asexual reproduction of Bourbon Street as accomplished when vegetative cuttings were taken from e initial selection in Suba, Colombia in October of 1989, mediately after selection, by technicians working under pervision of Cornelis P. VandenBerg.

Horticultural examination of controlled flowerings of ccessive plantings has shown that the unique combination characteristics as herein disclosed for Bourbon Street are mly fixed and are retained through successive generations asexual reproduction.

Bourbon Street has not been observed under all possible vironmental conditions. The phenotype may vary signifi-ntly with variations in environment such as temperature, ght intensity and daylength, without, however, any vari-ice in genotype.

The following observations, measurements and compari-ns describe plants grown in Suba, near Bogota, Colombia, nder greenhouse conditions which approximate those gen-ally used in commercial greenhouse practice.

The following traits have been repeatedly observed and e determined to be basic characteristics of Bourbon Street, which, in combination, distinguish this carnation as a new and distinct cultivar:

1. Commercial double flower type.
2. Flat flower form.
3. Cerise-cherry flower color.
4. Diameter of flower of 77 to 84 mm when fully opened, when grown as a disbudded carnation.
5. Rounded petals, with serrated and slightly ruffled petal margins.
6. Heavy, strong stems.
7. Relatively fast flowering response of 23 to 26 weeks after planting rooted cuttings.
8. Tolerant to resistant to *Fusarium oxysporum.*
9. High percentage of long to very long flowering stems from 45 to over 65 cm in length.
10 Recommended as a standard (disbudded) carnation.

The accompanying photographic drawing shows a typical inflorescence of Bourbon Street, grown as a disbudded cut carnation, with the colors being as nearly true as possible with illustrations of this type.

Of the commercial cultivars known to the inventor, the most similar in comparison to Bourbon Street is the cultivar Castellaro. Similar traits are flower color, and the recommendation to grow as a disbudded carnation. When compared with Castellaro, Bourbon Street has a larger flower by 2 to 10 mm, more finely serrated petal margins, and is more richly colored with better color retention than Castellaro. The calyx of Bourbon Street has 5 lobes, while the calyx from Castellaro has 6 to 7 lobes. Bourbon Street has superior resistance to *Fusarium oxysorum* than does Castellaro.

In the following description color references are made to The Royal Horticultural Society Colour Chart. The color values were determined on plant material grown as disbudded carnations at Suba, Colombia, and shipped to Salinas, Calif., on Jan. 25, 1996.

Classification:

*Botanical.*—*Dianthus caryophyllus* L. cv Bourbon Street.

*Commercial.*—Standard carnation for cut flower production.

INFLORESCENCE

*Form.*—Flat.

*Type.*—Commercial double.

*Flower diameter.*—77 to 84 mm when fully opened.

*Number of petals.*—65 to 72

*Color (general tonality from a distance of three meters)* .—Cerise-cherry.

*Color (upper surface).*—Margin 61C center 58B, base white with 149D.

*Color (under surface)*—Between 58B and 61C.

*Shape.*—Rounded, serrated, slightly ruffled.

*Calyx.*—5 lobed. Color between 144A and 144B.

*Androecium.*—Normal to semi-petaloid stamens; normal to degenerated anthers; moderate pollen.

*Gynoecium.*—Typical carnation, smooth, conical ovaries; 2 to 3 styles.

*Fragrance.*—Little to no fragrance.

*Fertility.*—Functions as both seed parent and pollen parent.

*Keeping quality.*—14 to 21 days after cutting and transportation.

PLANT

A. General appearance:

*Growth.*—Bushy, semi erect perennial; plant is normally pinched approximately three weeks after planting to produce upright habit typical of cut carnations.

*Branching.*—Semi-erect, numerous and unrestricted at base of plant; 3 to 5 laterals developing per stem.

*Height.*—Two (2) year old plants may reach 150 to 200 cm in height.

B. Foliage:

*Color.*—Typical carnation, between 136A and 189A, overlaid with 189B.

*Texture.*—Surface has a thin wax-like bloom which is bluish green in color.

*Size.*—Mature leaves are 8.5 to 22 cm in length and 6 to 12 mm in width; weakly curled.

*Shape.*—Long, narrow, lancet shaped.

C. Flowering: The first flush of flowers appears 23 to 26 weeks after planting rooted cuttings, and there are approximately 3 to 5 flowering stems at first flush when the apical bud is removed. The side laterals then grow out in approximately 8 to 9 weeks, after which the second flush of flowers appears. The flowers of the first and second flushes are similar in size, but in subsequent flushes the flowers tend to become somewhat smaller. There are approximately 6 to 7 flushes of flowers during a two year plant life, at which time a commercial plant would typically be discarded.

What is claimed is:

1. A new and distinct carnation plant named Bourbon Street, as described and illustrated.

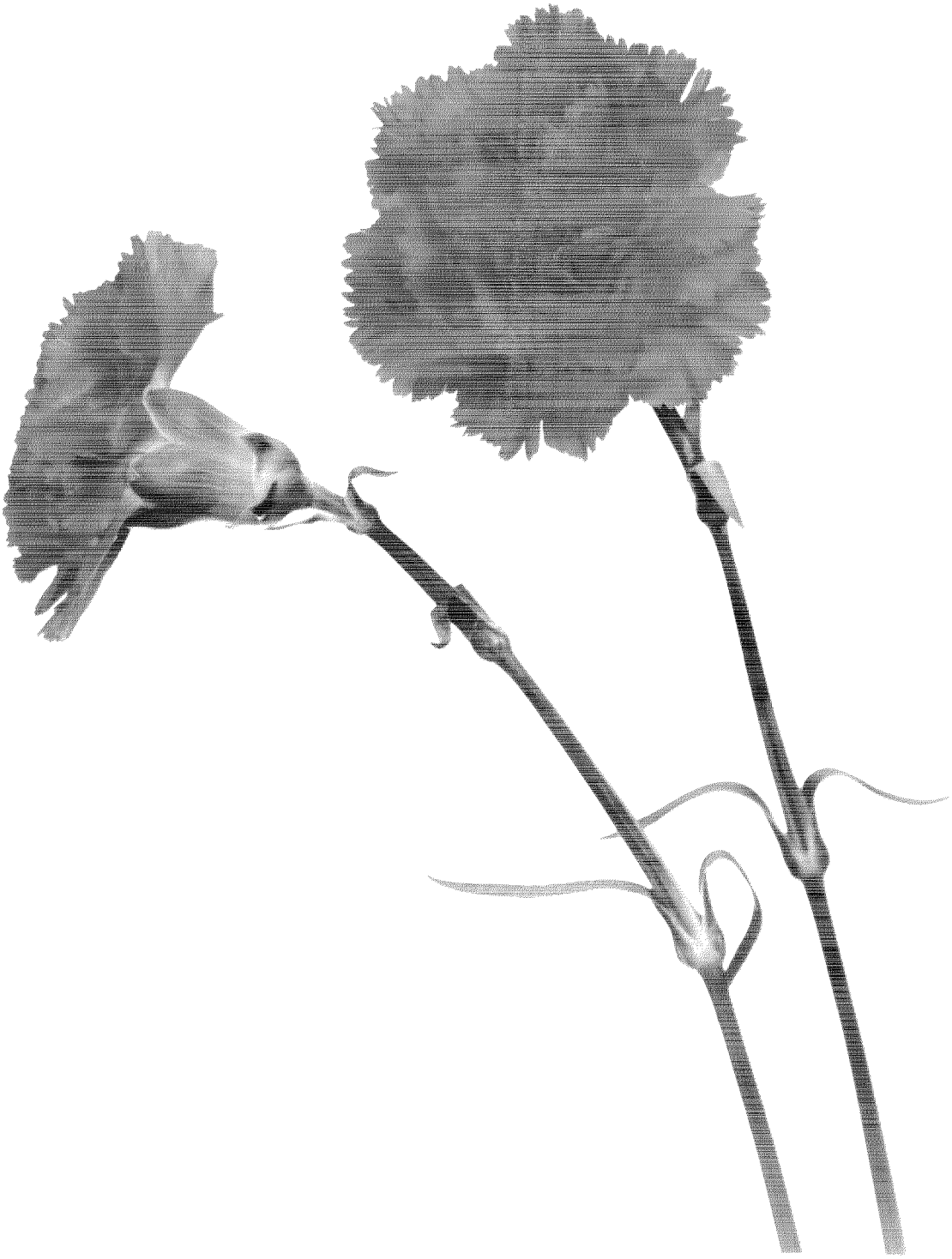

* * * * *